US012331091B2

(12) United States Patent
Teng et al.

(10) Patent No.: US 12,331,091 B2
(45) Date of Patent: Jun. 17, 2025

(54) CHIMERIC SIGNAL PEPTIDES FOR PROTEIN PRODUCTION

(71) Applicant: Taiwan Bio-Manufacturing Corporation, Taipei (TW)

(72) Inventors: Chao-Yi Teng, Taipei (TW); Ying-Ju Chen, Taipei (TW)

(73) Assignee: Taiwan Bio-Manufacturing Corporation, Taipei (TW)

( * ) Notice: Subject to any disclaimer, the term of this patent is extended or adjusted under 35 U.S.C. 154(b) by 970 days.

(21) Appl. No.: 17/417,112

(22) PCT Filed: Dec. 23, 2019

(86) PCT No.: PCT/US2019/068406
§ 371 (c)(1),
(2) Date: Jun. 22, 2021

(87) PCT Pub. No.: WO2020/139855
PCT Pub. Date: Jul. 2, 2020

(65) Prior Publication Data
US 2021/0388046 A1    Dec. 16, 2021

Related U.S. Application Data

(60) Provisional application No. 62/784,497, filed on Dec. 23, 2018.

(51) Int. Cl.
*C07K 14/00* (2006.01)
*C07K 14/47* (2006.01)
*C07K 14/705* (2006.01)
*C07K 16/00* (2006.01)
*C12N 9/16* (2006.01)

(52) U.S. Cl.
CPC ...... *C07K 14/4728* (2013.01); *C07K 14/4723* (2013.01); *C07K 14/70503* (2013.01); *C07K 16/00* (2013.01); *C12N 9/16* (2013.01); *C12Y 301/03001* (2013.01); *C07K 2317/14* (2013.01); *C07K 2319/02* (2013.01)

(58) Field of Classification Search
CPC ............ C07K 14/4728; C07K 14/4723; C07K 14/70503; C07K 2319/02; C07K 14/00
See application file for complete search history.

(56) References Cited

U.S. PATENT DOCUMENTS 8,241,870 B2 * 8/2012 Young .................... C12N 15/85
530/300
8,883,450 B2  11/2014 Fontayne

OTHER PUBLICATIONS

Kober et al., "Optimized Signal Peptides for the Development of High Expressing CHO Cell Lines", pp. 1164-1169, Jan. 17, 2013, Biotechnology and Bioengineering.
Haryadi et al., "Optimization of Heavy Chain and Light Chain Signal Peptides for High Level Expression of Therapeutic Antibodies in CHO Cells", pp. 2-3, 6, 8 and 13, Feb. 23, 2015, Plos One.

* cited by examiner

*Primary Examiner* — Jeanette M Lieb
(74) *Attorney, Agent, or Firm* — NZ Carr Law Office

(57) ABSTRACT

A chimeric signal peptide for protein expression includes an N-region, a hydrophobic region, and a C-region, wherein the N-region and the C-region are from a same signal peptide of a first protein and the hydrophobic region is from a signal peptide of a second protein, wherein the first protein is different from the second protein. The first and second protein are independently selected from the group consisting of BM40, IL2, HA, Insulin, CD33, IFNA2, IgGK leader, AZU, and SEAP.

2 Claims, 14 Drawing Sheets
Specification includes a Sequence Listing.

Query Sequence: >Unknown Sequence
MPLLLWVLLLWAGALA...

Significant Alignments:

| Name | Bitscore | SValue |
|---|---|---|
| CD33_HUMAN (Signal Peptide - Potential.) | 28.1 | 100.0 |
| LTBP1_RAT (Signal Peptide - Potential.) | 23.9 | 5.5 |
| LTBP1JKXJSE (Signal Peptide - Potential.) | 23.9 | 5.5 |
| LTBP1_HUMAN (Signal Peptide - Potential.) | 23.9 | 5.5 |
| C0MA1_HUMAN (Signal Peptide - Potential.) | 23.9 | 5.5 |
| E 3A9JOJSE (Signal Peptide) | 23.9 | 5.5 |
| KV3A6_M0USE (Signal Peptide) | 23.9 | 5.5 |
| C05A1_MOUSE (Signal Peptide - Potential.) | 23.1 | 3.2 |
| GLMP_FONAB (Signal Peptide - Potential.) | 22.7 | 2.4 |
| GLMP_HUMAN (Signal Peptide - Potential.) | 22.7 | 2.4 |

Insignificant Alignments:

Most Significant SValue:
>CD33_HUMAN (Cleavage Site after AA 17)
        Length = 60

Score = 28.1 bits (61).  Expect = 0.60
Identities = 13/16 (81$), Positives = 14/16 (87$)
Query: 1    MPLLWVLLLWAGALA...
            MPLLL + LLWAGALA
Sbjct: 1    MPTJJJPLLWAGALA 16
              /\

Result : Signal Peptide, putative Cleavage Site after AA 17 ( by similarity to CD33_HUMAS)

FIG. 3D

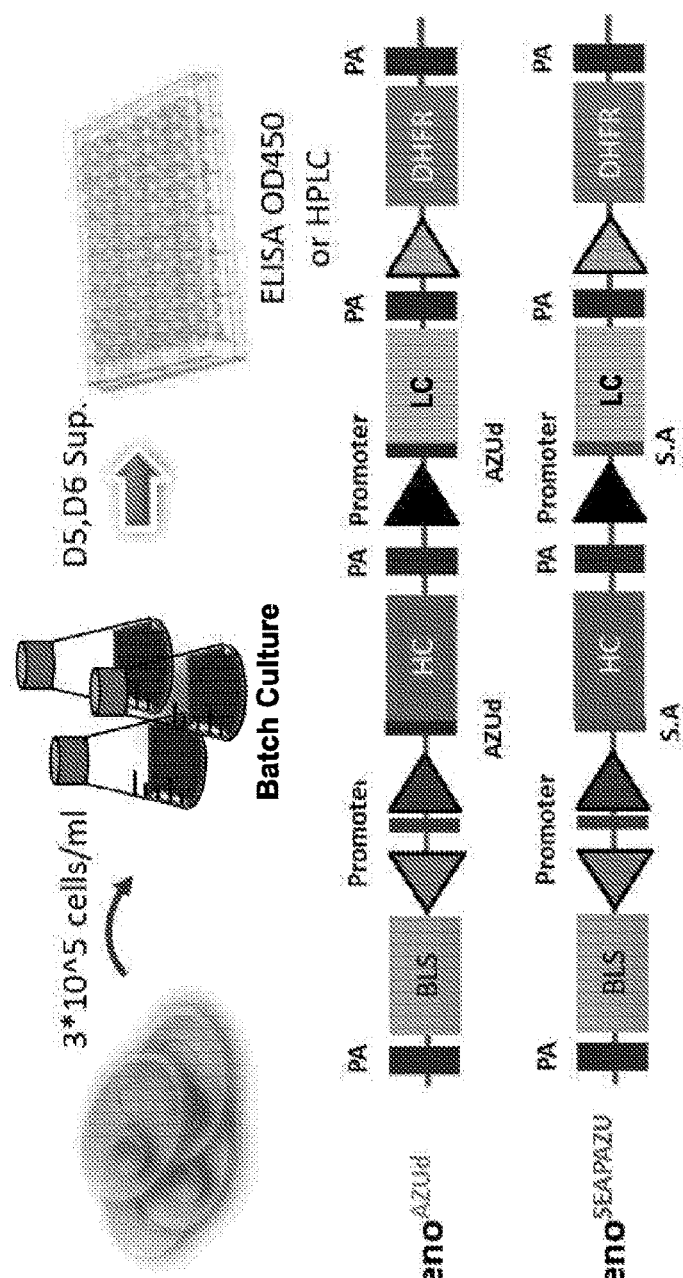
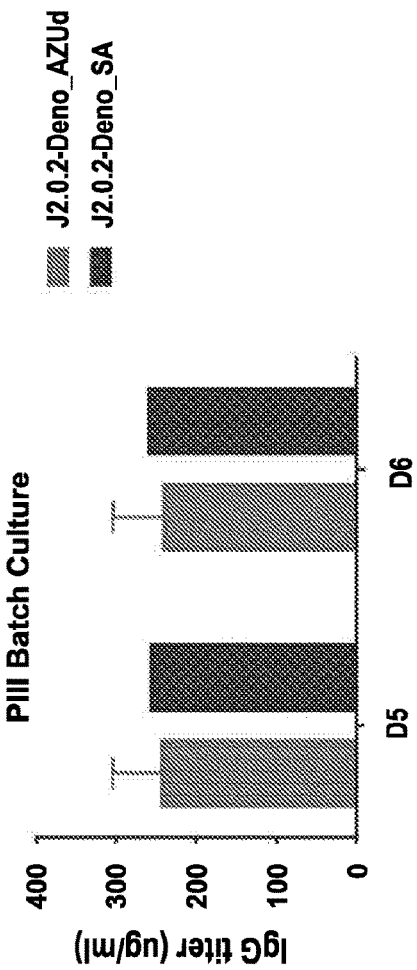
FIG. 10A
FIG. 10B
FIG. 10C

CHIMERIC SIGNAL PEPTIDES FOR PROTEIN PRODUCTION

BACKGROUND OF INVENTION

Field of the Invention

The invention relates generally to preparation of therapeutic proteins. In particular, the invention relates to application of artificial signal peptides to optimize the protein expression.

Background Art

Developing stable cell lines such as CHO to produce high levels of proteins or antibodies is a trend of the industry. In the past, optimization of mammalian expression systems mainly focuses on the downstream processes and media developments. However, to meet needs for high yields, faster development, and lower production costs, one needs to consider optimization of expression vectors and other components as well. When producing secretory proteins, a rate-determining step affecting protein secretion is the step of protein translocation into the lumen of the endoplasmic reticulum. This is determined by the sequences of secretion signals, i.e., signal peptides (SPs). Numerous studies showed that the endogenous SPs of the original proteins or antibodies are usually not optimized, and there is still unmet need for improvement.

A signal peptide is a short, generally 5-30 amino acids long, peptide present at the N-terminus of most newly synthesized proteins, including those that are secreted from the cells, reside inside certain organelles (Golgi or endoplasmic reticulum), or are inserted into cellular membranes.

A signal peptide consists of an N-region, a hydrophobic region (H-region) and a C-region. The H-region of the signal peptide contains a stretch of hydrophobic amino acids (about 5-16 residues long) that tends to form a single alpha-helix. The N-region of many signal peptides contain a short stretch of positively charged amino acids, which may help to enforce proper topology of the polypeptide during translocation by what is known as the positive-inside rule. At the C-region of a signal peptide, there is typically a stretch of amino acids that is recognized for cleavage by signal peptidases. However, the protease cleavage site is absent from transmembrane domains that serve as signal anchor peptides, which are sometimes referred to as signal anchor sequences.

Many studies found that the native signal peptides (SPs) of most proteins are not optimal, and optimizing SPs or replacing native SPs with alternative SPs may lead to increased productions of target proteins. For example, L. Kober et al. showed that better antibody expressions were obtained with natural signal peptides derived from human albumin and human azurocidin (AZU) (Biotechnol. Bioeng., 2013 April; 110(4):1164-73. doi: 10.1002/bit.24776).

SUMMARY OF INVENTION

Embodiments of the invention relates to chimeric signal peptides. A chimeric signal peptide for protein expression includes an N-region, a hydrophobic region, and a C-region, wherein the N-region and the C-region are from the signal peptide of a first protein and the hydrophobic region is from the signal peptide of a second protein, wherein the first protein is different from the second protein.

In accordance with some embodiments of the invention, the first and second proteins may be independently selected from the group consisting of BM40, IL2, HA, Insulin, CD33, IFNA2, IgK, AZU, and SEAP.

One aspect of the invention relates to methods for producing a target protein or antibody using a chimeric signal peptide of the invention. A method in accordance with one embodiment of the invention comprises: transfecting a mammalian host cell with an expression cassette that includes a chimeric signal peptide of the invention; culturing the mammalian host cell to express the target protein; and harvesting the target protein.

Other aspects and advantages of the invention will be apparent from the following description and the appended claims.

BRIEF DESCRIPTION OF DRAWINGS

FIG. 3D shows results of BLAST prediction of the chimeric CD33_IgK signal peptide. By sequence homology comparison, BLAST also predicts that the signal peptidase would cleave after the alanine (A) and before the glutamic acid (E) in MPLLLWVLLLWAGALA-EVQLVESGGG (SEQ ID NO:11).

FIG. 7 also shows that proper sequence of the chimeric signal peptide is important. For example, the BMCD variant with the last two residues (LA) deleted is a much weaker signal peptide.

FIG. 10A shows a scheme illustrating the protocols of cell culture and protein production. FIG. 10B shows two expression vectors for the production of Denosumab using AZUd and SEAPAZU signal peptides, respectively. FIG. 10C show the results of Denosumab productions using the expression vectors of FIG. 10B.

DETAILED DESCRIPTION

Figure 1:
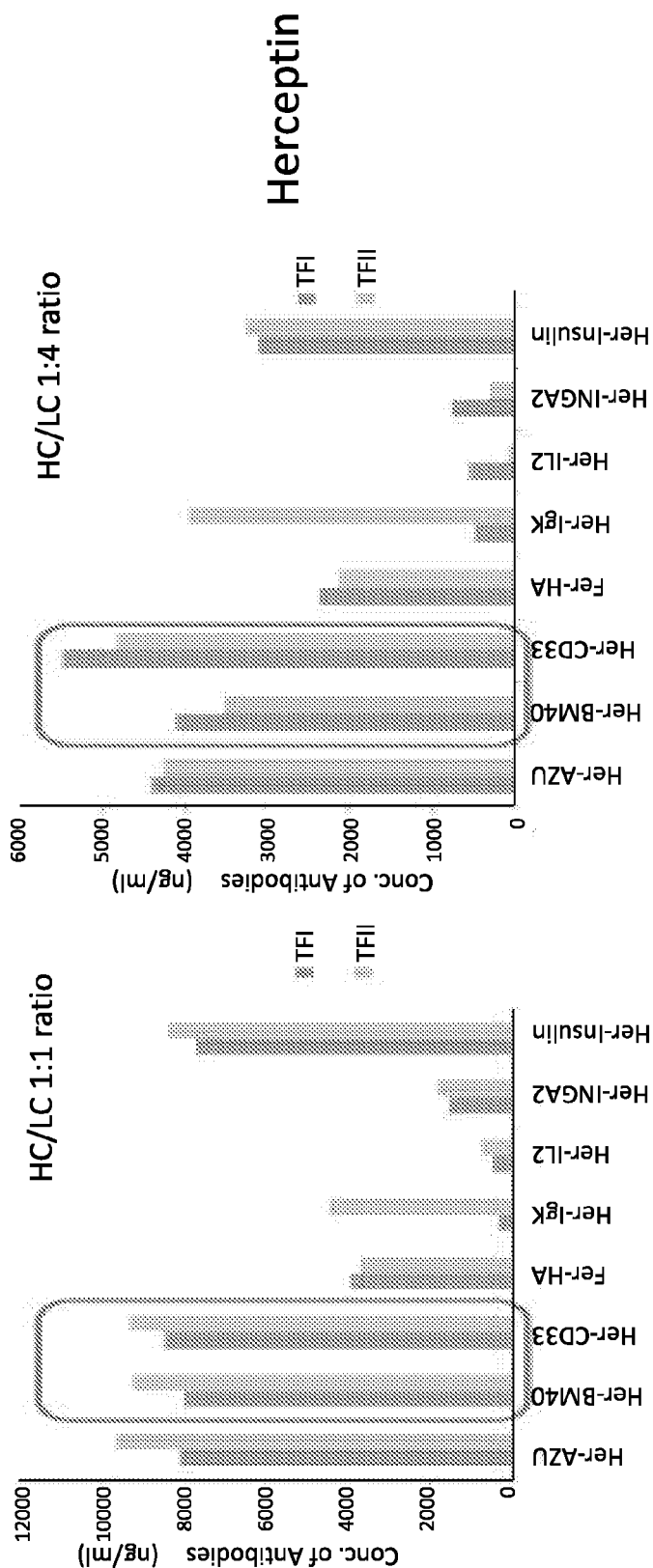
FIG. 1 shows efficiencies of various common signal peptides in the enhancements of the production of Herceptin at different HC/LC ratios.

Embodiments of the invention relate to chimeric signal peptides and their uses to enhance the productions of target proteins from eukaryotic systems. In accordance with embodiments of the invention, chimeric signal peptides are designed to enhance the expression and/or secretion of target proteins expressed in eukaryotic host cells. A signal peptide typically contains 5-30 amino acids in length and can be divided into an N-region, an H-region (hydrophobic region), and a C-region. A chimeric signal peptide of the invention may be constructed, for example, by swapping the hydrophobic region of a first signal peptide with the hydrophobic region from a second signal peptide.

The chimeric signal peptides of the invention may be based on known signal peptides. Commonly used signal peptides include those from BM40 (basement membrane protein 40), IL-2 (interleukin 2), HA (hemagglutinin), Insulin, CD33, IFNA2 (interferon alpha 2), IgK (immunoglobulin kappa chain), SEAP (secreted alkaline phosphatase), and AZU (Azurocidin) proteins. In the following description, these protein names may be also used to refer to their signal peptides (SPs). From these natural signal peptides, better ones are selected for further optimization. To assess the efficiencies of these signal peptides in enhancing protein productions, one can construct an expression vector containing the signal peptide and assay for levels of protein expression, e.g., using ELISA or other assays. The following examples will use antibodies as examples of target proteins. However, one skilled in the art would appreciate that embodiments of the invention may be used to express any proteins, not just antibodies.

Using an antibody as a target protein, two vectors containing a heavy chain and a light chain, respectively, of an antibody are cloned. Alternatively, an expression vector containing both the heavy chain and light chain may be used. To facilitate the assays, these vectors may also contain tags (e.g., a red and a green fluorescence tags, respectively). The test signal peptide is integrated in front of the translation start codon ATG of the antibody heavy chain or light chain. The efficiencies of antibody productions were then evaluated by co-transfection of these vectors into proper host cells. Several signal peptides, such as Albumin (ALB), Azurocidin (AZU), H5L1, and H7N1 that are known to support efficient protein productions, may be used as positive controls.

For protein productions, constructs that contain the signal peptides of the invention may be constructed into any suitable expression vectors appropriate for the protein expression systems (e.g., *E. coli*, yeast cells, CHO, etc.). For example, in our prior study, suitable expression vectors J1.0delta and J1.0.2 (based on pTCAE8.3) were constructed for the productions of Herceptin and Avastin. The signal peptide of each vector is AZU (Azurocidin) or Ori (original). To find better signal peptides, the AZU and Ori in the independent vectors containing the nucleic acid sequences of heavy chain or light chain, respectively, may be replaced with other signal peptides. In one example, a total of 32 vectors were constructed, and each contains a light chain or a heavy chain of an antibody (e.g., Herceptin or Avastin) with a different signal peptide.

These expression vectors were transiently transfected into CHO cells (e.g., DXB11 cells, or CHOK1 (CCL61-S1) cells) with different heavy-chain (HC) to light-chain (LC) ratio (1:1 or 1:4) to assess transfection/expression efficiencies. The expression levels of the antibodies were then assessed using ELISA.

As shown in FIG. 1, using Herceptin as a target protein, the constructs with BM40 and CD33 as the signal peptides produced yields that are comparable to or better than the positive control using AZU as the signal peptide. In addition, FIG. 1 shows that the titer could reach 8 to 9 µg/ml with a HC/LC ratio of 1:1 and could reach 4 to 5.5 µg/ml with a HC/LC ratio of 1:4. Therefore, in this example, a higher yield is produced with an HC/LC ratio of 1:1.

Figure 2:
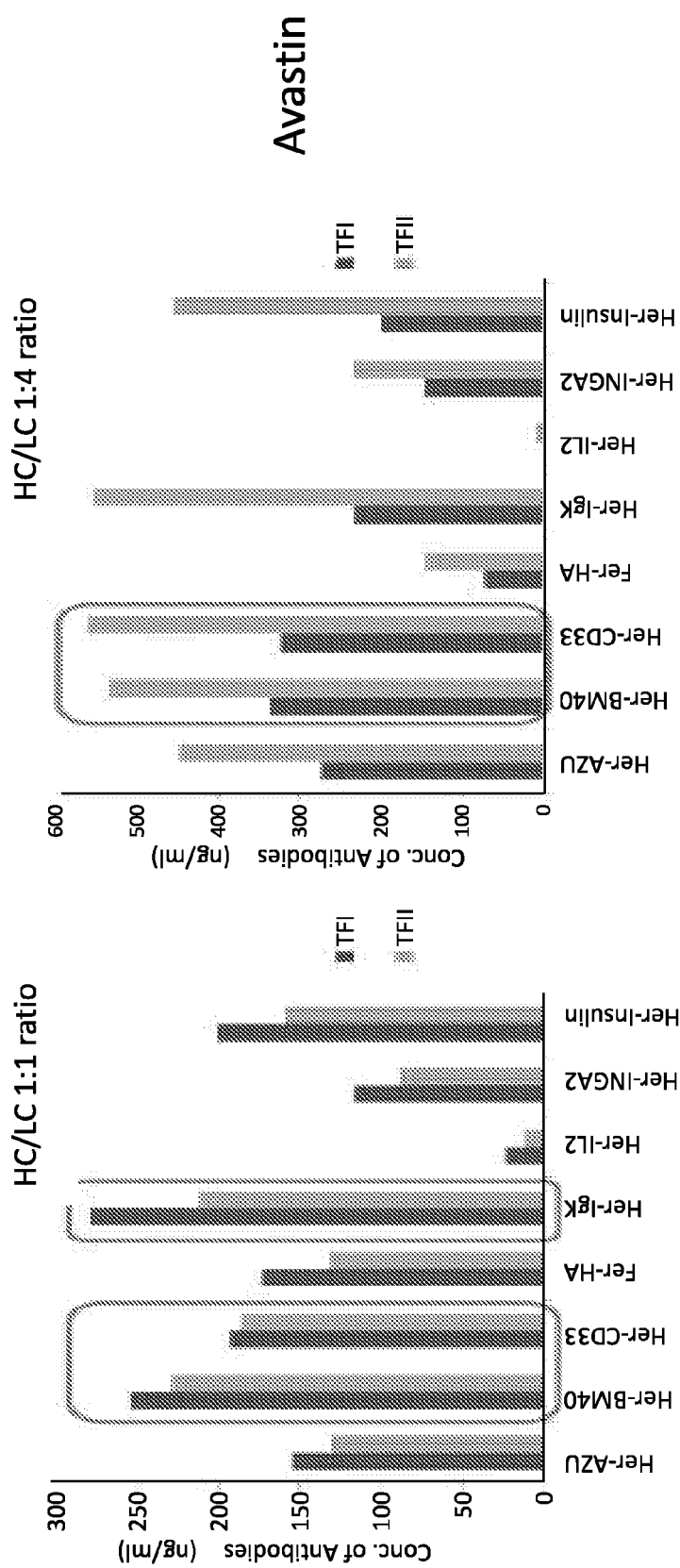
FIG. 2 shows efficiencies of various common signal peptides in the enhancements of the production of Avastin at different HC/LC ratios.

Next, we applied different signal peptides to produce Avastin. As shown in FIG. 2, the constructs with BM40, CD33, and IgK signal peptides produced yields higher than the construct with original signal peptide (ORI). The protein expression levels with BM40, CD33, and IgK signal peptides are comparable to or better than the positive control (AZU). Different transfection ratios (HC/LC=1:1 or 1:4) produced a difference in the yields. The titer is 200-250 ng/ml when HC/LC=1:1, and the titer reaches 300-550 ng/ml when HC/LC=1:4. Thus, in this example, 1:4 ratio produced more proteins.

Based on these and similar tests, several signal peptides are found to have similar or better abilities, as compared to the positive control AZU, to enhance protein expressions. These signal peptides are selected for further optimization. These selected signal peptides include CD33, IgK, BM40, AZU, and SEAP signal peptides.

As noted above, a signal peptide may be divided into three regions: the N-region, the H-region (hydrophobic region), and the C-region. The hydrophobic region (H-region) of a signal peptide forms a helix that is important for interactions with a signal recognition particle (SRP). Such interactions allow an SRP to bind the nascent protein and facilitate the translocation of the protein across the ER membrane. Because the H-regions play such important functions, we decided to investigate whether changing the H-regions can improve the efficiencies of signal peptides.

One approach of the invention is to create chimeric signal peptides, in which the H-region of the first signal peptide is replaced with a corresponding H-region from a second signal peptide. To perform such H-region swapping, we first analyzed the signal peptides to determine the boundaries of each regions and the signal protease cleavage sites. Many methods/programs are available in the art for such analysis, e.g., SignalP 4.0, SignalP-HMM, PrediSi, and Signal Blast.

For example, SignalP server, hosted by the Center for Biological Sequence Analysis at the Technical University of Denmark, predicts the presence and location of signal peptide cleavage sites in amino acid sequences. The method incorporates a prediction of cleavage sites and a signal peptide/non-signal peptide prediction based on a combination of several artificial neural networks. In addition, the server provides methods for predicting N-region, H-region, and C-region.

Figure 3A:
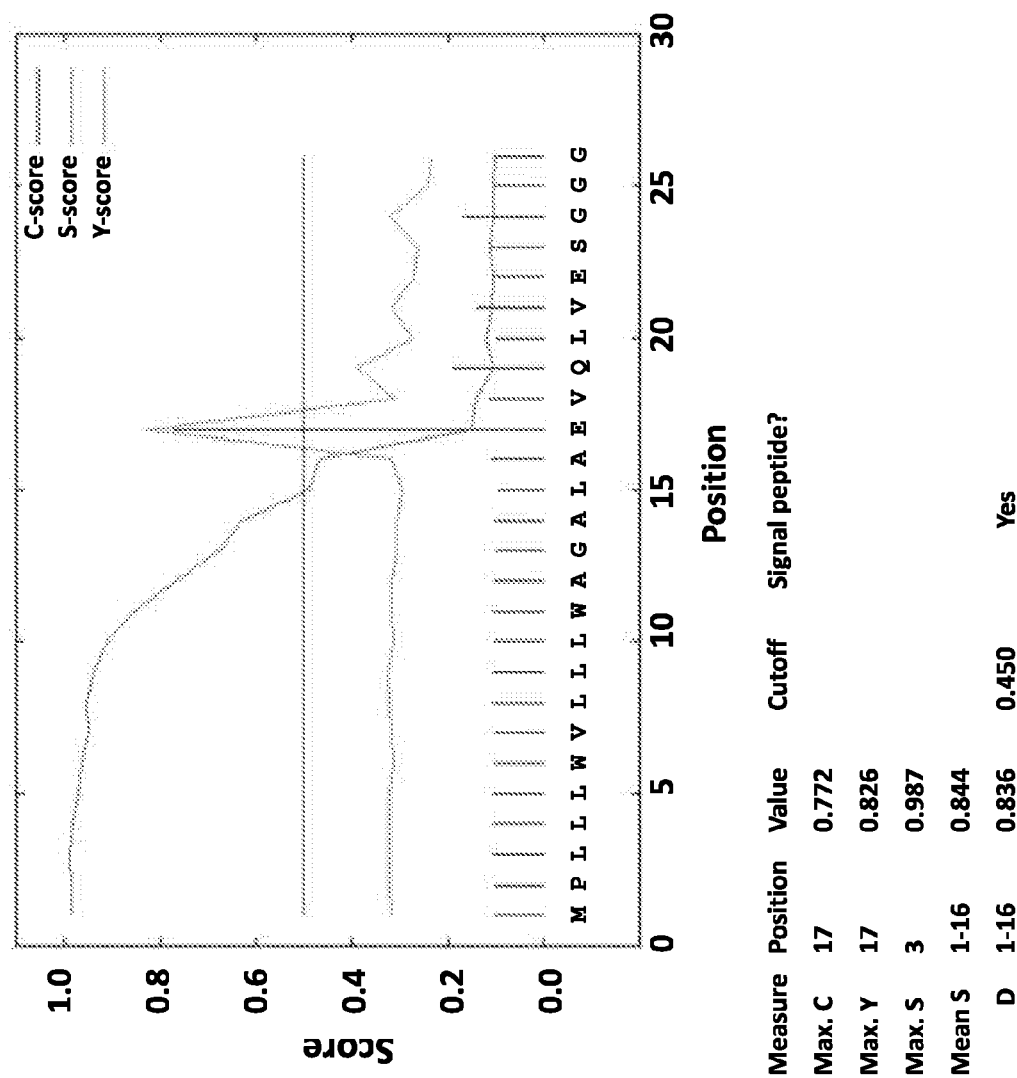
FIG. 3A shows results of SignalP 4.0 prediction of the chimeric CD33_IgK signal peptide. SignalP 4.0 predicts the C, S, Y scores. and based on these scores. The C score predicts that the signal peptidase would cleave after the alanine (A) and before the glutamic acid (E) in the sequence, MPLLLWVLLLWAGALA-EVQLVESGGG (SEQ ID NO:11).

Using a CD33_IgK chimeric signal peptide as an example, MPLLLWVLLLWAGALA-EVQLVESGGG (SEQ ID NO:11), SignalP 4.0 predicts the C, S, Y scores. The C score predicts that the signal peptidase would cleave after the alanine (A) and before the glutamic acid (E) in the sequence, MPLLLWVLLLWAGALA-EVQLVESGGG (SEQ ID NO:11). The S score indicates the likelihood of the sequence being a signal peptide: the higher the score means it is more likely to be a signal peptide. The Y score is based on a combination of the C and S scores. The Y score further confirms that the peptidase would cleave before the glutamic acid residue. (see FIG. 3A).

Figure 3B:
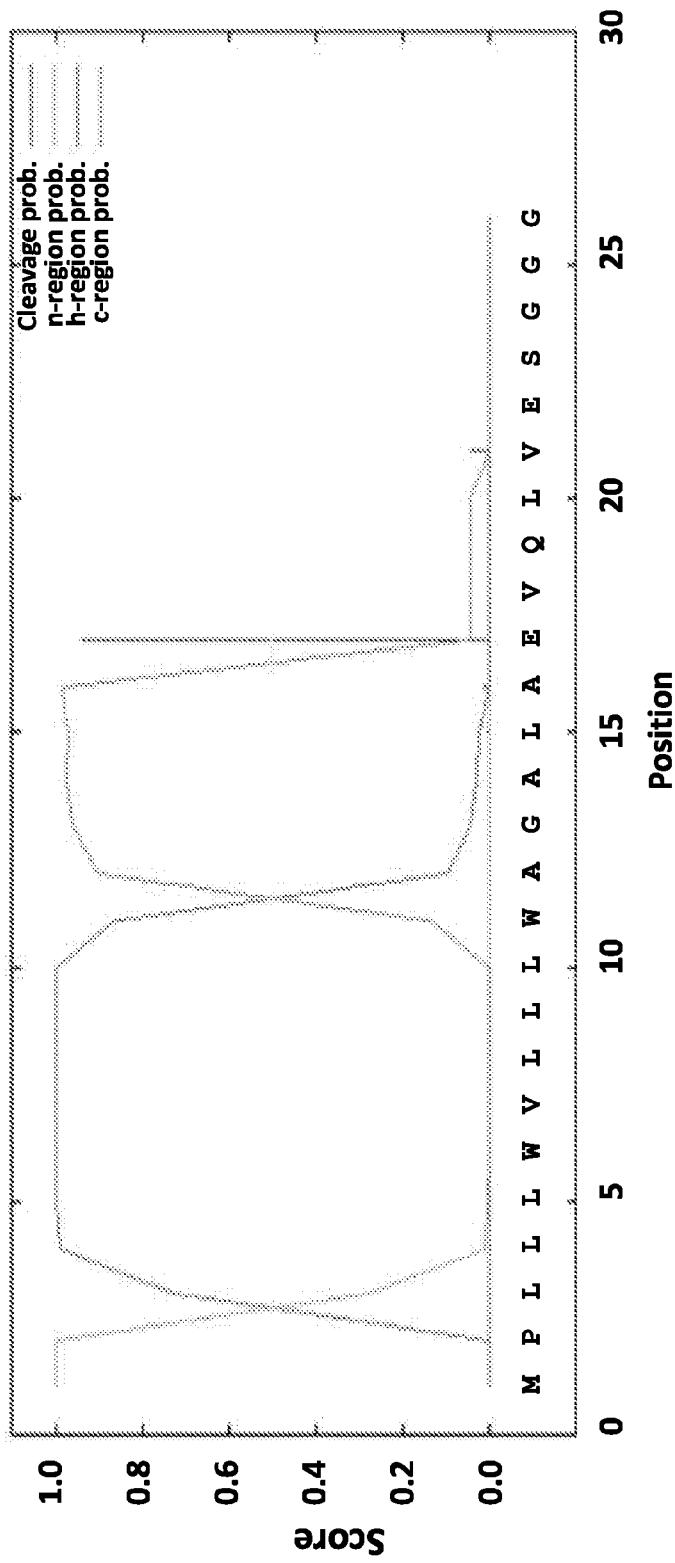
FIG. 3B shows results of SignalP-HMM prediction of the chimeric CD33_IgK signal peptide. SignalP-HIMM predicts the N-region, H-region, and C-region of the signal peptide. Signal-HMM also predicts that the signal peptidase would cleave after the alanine (A) and before the glutamic acid (E) in MPLLLWVLLLWAGALA-EVQLVESGGG (SEQ ID NO:11).

A similar program, SignalP-HMM (based on hidden Markov Model, Henrik Nielsen and Anders Krogh, In *Proceedings of the Sixth International Conference on Intelligent Systems for Molecular Biology* (ISMB 6), AAAI Press, Menlo Park, California, pp. 122-130 (1998)), also predicts the N-region, H-region, and C-region, as well as the signal peptidase cleavage site (FIG. 3B). This program also predicts that the peptidase will cleave before the glutamic acid, consistent with the SignalP 4.0 prediction.

Figure 3C:
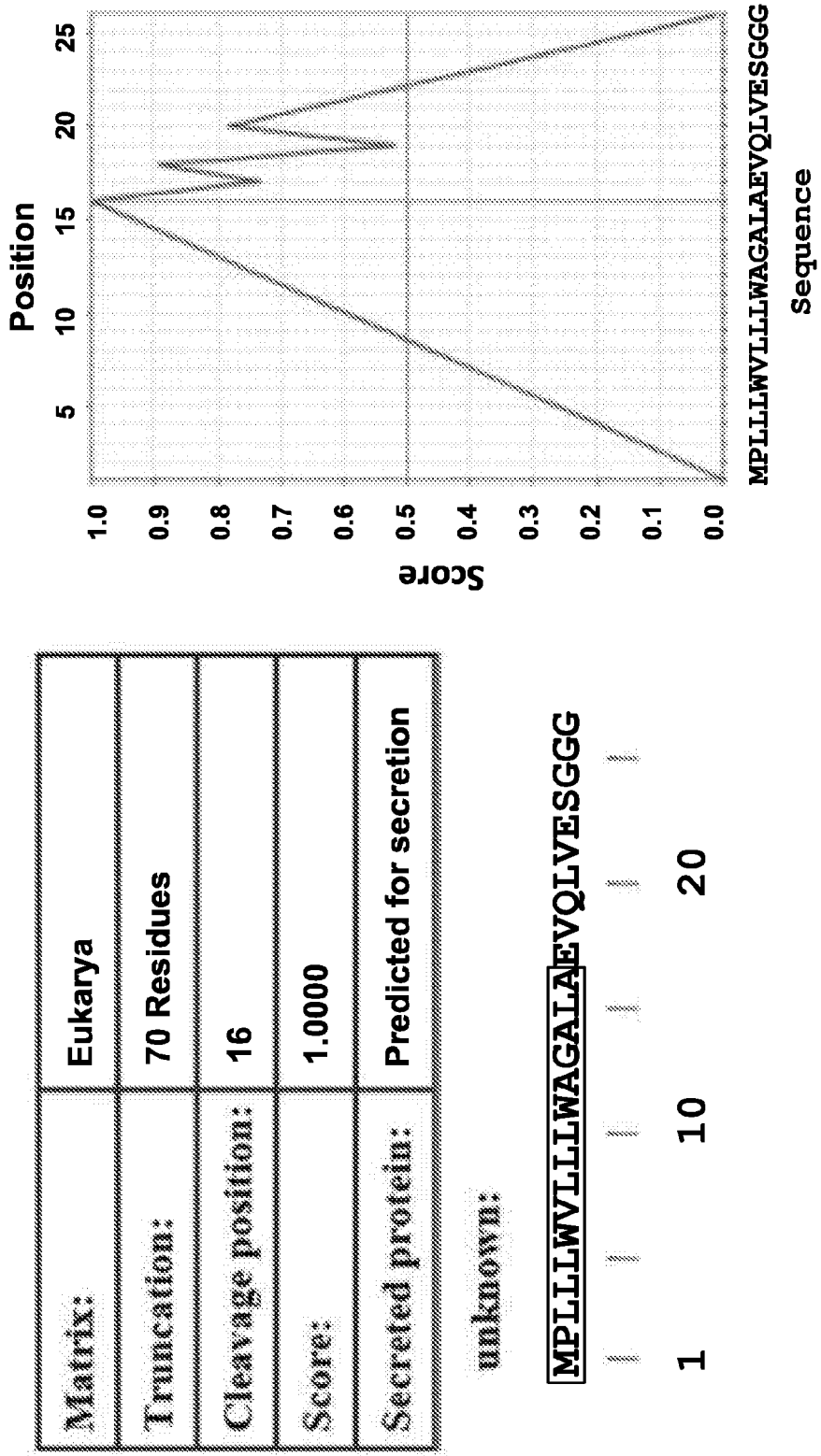
FIG. 3C shows results of PrediSi prediction of the chimeric CD33_IgK signal peptide. PrediSi also predicts that the signal peptidase would cleave after the alanine (A) and before the glutamic acid (E) in MPLLLWVLLLWAGALA-EVQLVESGGG (SEQ ID NO:11).

Another program, PrediSi (Prediction of Signal Peptides, Karsten Hiller et al. "*Prediction of Signal Peptides and Their Cleavage Positions*," Nucleic Acids Res., 2004, July 1, 32:: W375-W379, doi: 10.1093/nar/gkh378), also predicts that the peptidase will cleave between alanine (A) and glutamic acid (E). (FIG. 3C). Finally, BLAST program can also be used to predict the cleavage site by homology comparison with other known signal peptide cleavage sites. (FIG. 3D).

Any of these methods may be used to predict the signal peptides and their corresponding N-regions, H-regions, and C-regions. They generally produce consistent results. Even if, arguendo, there is minor discrepancy, the precise demarcation of boundaries between the N-regions, H-regions, and C-regions are not critical for embodiments of the invention. As noted above, the H-region is a hydrophobic stretch that tends to form an α-helix. It is known that the M domain of a signal recognition particle (SRP) binds signal peptides with considerable sequence variations in the H-region, including a synthetic peptide with poly-Leu for its H-region. (Kendall et al., "Idealization of the hydrophobic segment of the alkaline phosphatase signal peptide," Nature, 1986; 321:706-708). Therefore, swapping one α-helix for another would not be impacted by the exact boundaries for the α-helix.

In accordance with embodiments of the invention, based on the above-mentioned prediction methods or other similar methods, one can design H-region swapping to create chimeric signal peptides. For example, one may swap the H-region of a first signal peptide with the H-region from a second signal peptide. Based on the promising signal peptides described above, e.g., CD33, IgK, BM40, AZU, and SEAP signal peptides, one can create various chimeric signal peptides.

In this description, the following notations are adopted for the chimeric signal peptides: the first signal peptide providing the N-region and C-region is listed first, followed by the name of the second signal peptide that provides the H-region. For example, BM40_CD33 (or BM-CD or BMCD) chimeric signal peptide contains the N-region and C-region from BM40 and the H-region from CD33. Similarly, CD33_BM40 (or CD-BM or CDBM) chimeric signal peptide contains the N-region and C-region from CD33 and the H-region from BM40. Other examples include: CD33_IgK (CD33 with the hydrophobic region of IgK leader), IgK_CD33 (IgK leader with the hydrophobic region of CD33), SEAP_AZU (SEAP with the hydrophobic region of AZU), AZU_SEAP (AZU with the hydrophobic region of SEAP). The nucleotide and peptide sequences for some of these chimeric signal peptides are shown in the following Table 1:

TABLE 1

| SP name | Sequences of Signal Peptides | SEQ ID NO |
| --- | --- | --- |
| CD33_IgK | MPLLLWVLLLWAGALA | 1 |
| IgK_CD33 | METDTLLLLLPLLWVPGSTG | 2 |
| SEAP_AZU | MILGPLTVLALLAGLLRLQLSLG | 3 |
| AZU_SEAP | MTRCMLLLLLLGLASSRA | 4 |
| BM40_CD33 | MRALLLLLPLLWAGRALA | 5 |
| CD33_BM40 | MPWIFFLLCLAGALA | 6 |
| SEAP | MILGPCMLLLLLLGLRLQLSLG | 7 |
| AZU | MTRLTVLALLAGLLASSRAGSSPLLD | 8 |
| AZUd | MTRLTVLALLAGLLASSRA | 9 |
| 3D5R SP | MRVPAQLLGLLLLWLPGARC | 10 |
| CD33-IgK-P | MPLLLWVLLLWAGALA-EVQLVESGGG | 11 |
| BM40_CD33-truncated | MRALLLLLPLLWAGRA | 12 |

Underlines indicate the hydrophobic regions in the chimeric signal peptides.

The following section will use a limited number of specific chimeric signal peptides as examples to illustrate embodiments of the invention. However, one skilled in the art would appreciate that these limited examples are for illustration only and are not meant to limit the scope of the invention.

These chimeric signal peptides can be first analyzed in silico using SignalP server (or other similar services) to make sure that they can still function as signal peptides, and they still have the signal peptidase cleavage sites. The following examples use BMCD and CDBM chimera as the signal peptides to illustrate embodiments of the invention. However, the description is equally applicable to other chimeric signal peptides of the invention.

Figure 4:
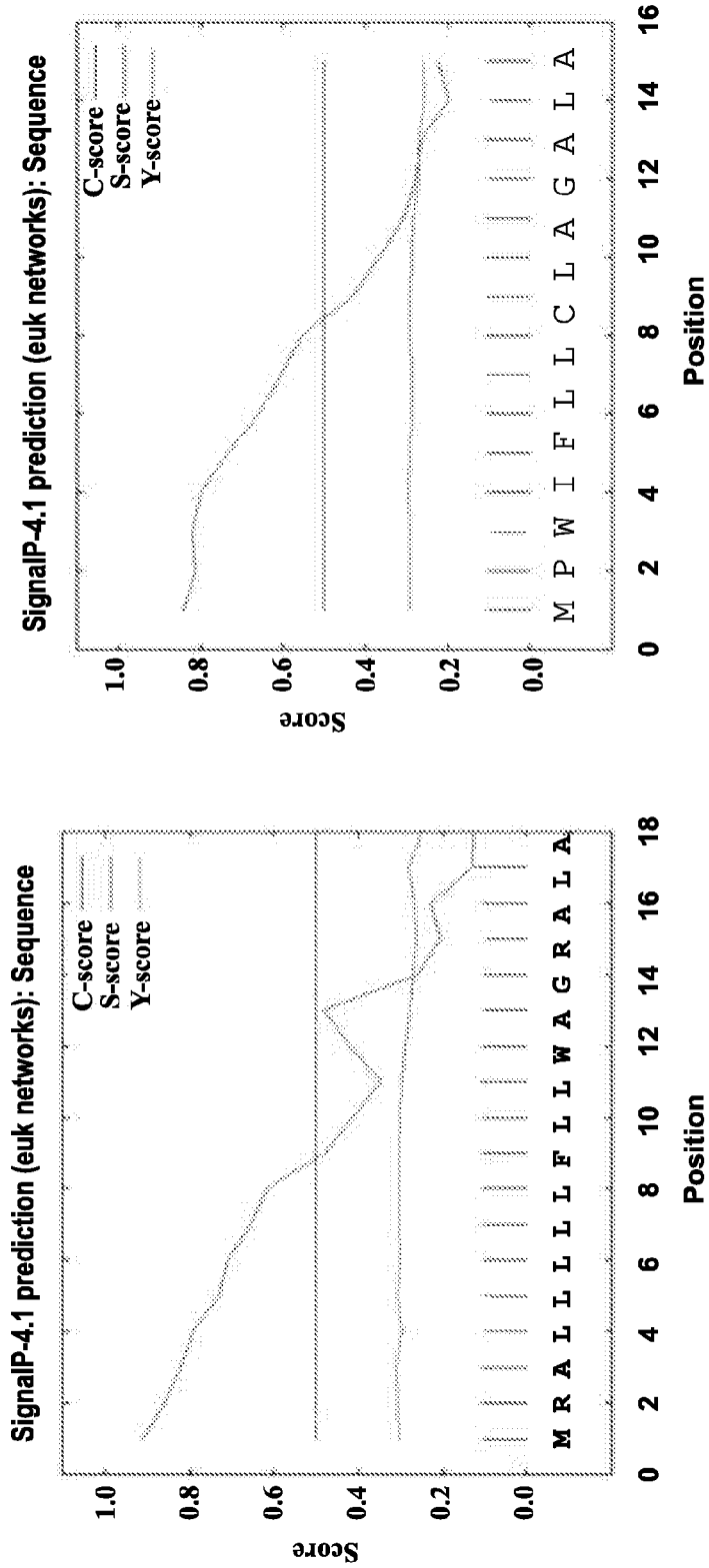
FIG. 4 shows that both chimeric signal peptides, BMCD and CDBM, have well defined signal peptidase cleavage sites, indicating such chimeric signal peptides likely would have their functions preserved.

As shown in FIG. 4, both chimeric signal peptides, BMCD and CDBM, have well defined signal peptidase cleavage sites, indicating such chimeric signal peptides likely would have their functions preserved. All other chimera, CDIgK, IgKCD, SEAPAZU, and AZUSEAP, are found to have similarly preserved signal peptidase cleavage sites.

These chimeric signal peptides are then tested for their abilities to serve as signal peptides and to assess their abilities to support and enhance protein expression/secretion. The tests are performed using an exemplary construct shown in FIG. 5.

Figure 5:
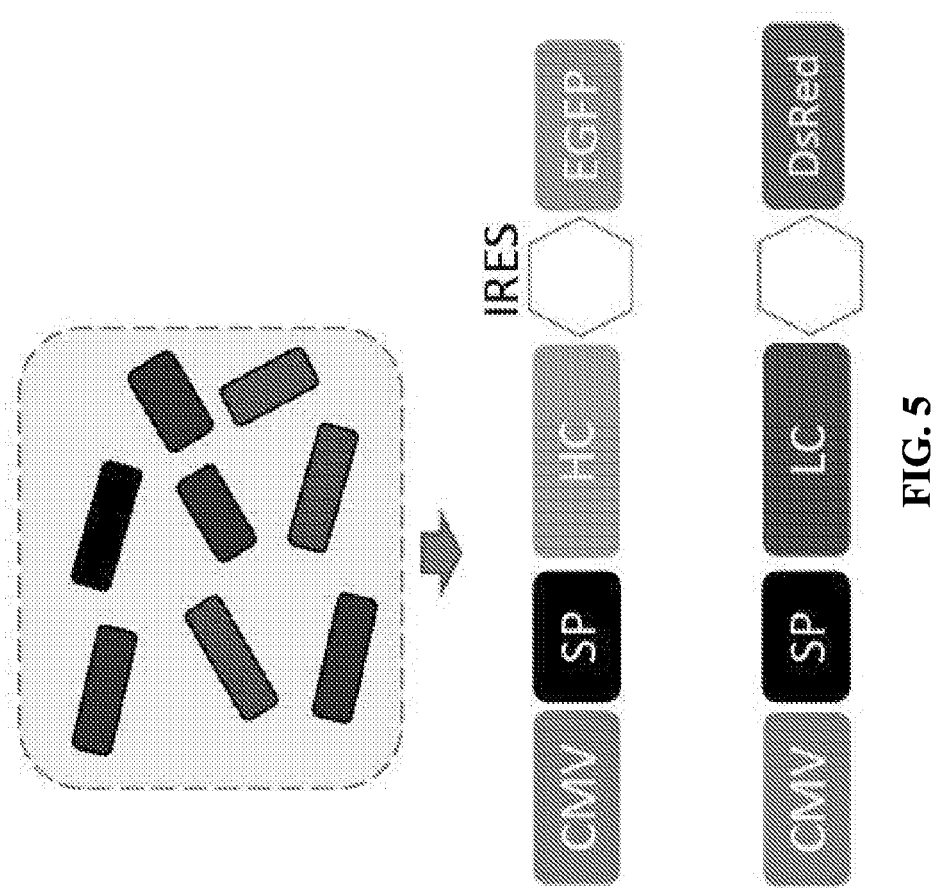
FIG. 5 shows a schematic illustrating the constructions of separate heavy-chain and light-chain expression vectors containing various signal peptide sequences of the invention.

As shown in FIG. 5, the chimeric signal peptides may be cloned into an expression vector for a heavy chain (HC) of an antibody and another expression vector for a light chain (LC) of the antibody, at the signal peptide (SP) locations. In this example, the expression vectors are under the control of a proper promoter (e.g., CMV promoter) and include an internal ribosome entry site (IRES) sequence for ribosome entry. The HC vector and the LC vector may be tagged with an enhanced green fluorescent protein (EGFP) and a Discosoma red fluorescent protein (DsRed), respectively, to facilitate the analysis. The two expression vectors are then co-transfected into host cells (e.g., CHO cells) for protein production. The amounts of protein produced may be analyzed with any suitable methods, such as ELISA.

Figure 6:
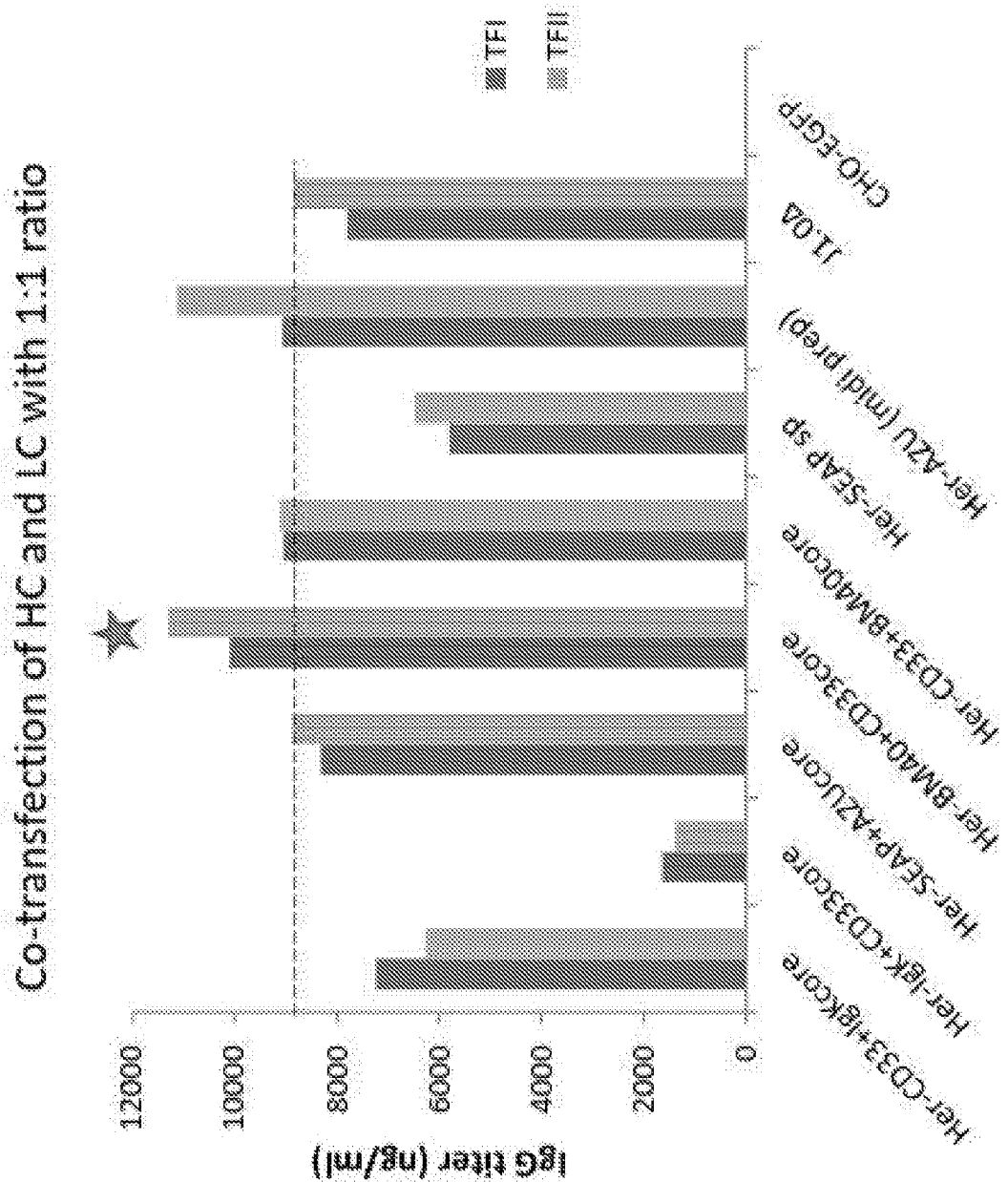
FIG. 6 shows results from various chimeric signal peptides of the invention. Several of these chimeric signal peptides can confer protein expression at levels comparable to or better than that of AZU. Among the better chimeric signal peptides, BMCD shows the best results.

Using Herceptin as a target protein, FIG. 6 shows results from various chimeric signal peptides (e.g., CD-IgK, IgK-CD, SEAP-AZU, AZU-SEAP, BM-CD, and CD-BM). Indeed, several chimeric signal peptides can confer protein expression at levels comparable to or better than that of AZU (positive control). Among the better chimeric signal peptides, BMCD shows the best results.

Figure 7:
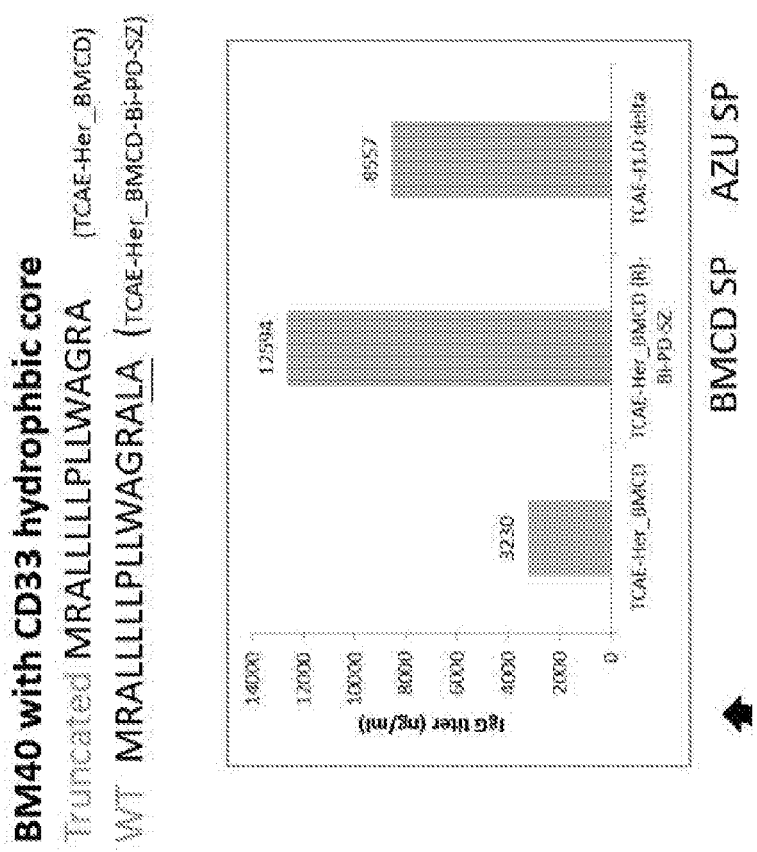
FIG. 7 shows that the BMCD chimeric signal peptide is significantly better than AZU. The expression level from BMCD is about 1.5× that of AZU.

The above results are from co-transfection of two separate vectors for the production of HC and LC chains of Herceptin. An alternative method is to construct an expression vector that produces both HC and LC from the same vector. To test whether the one-vector expression system would be more effective, the HC vector containing BMCD and the LC vector containing BMCD are subcloned into a proper expression vector (e.g., J2.0-PDSZ vector, which is based on pTCAE8.3). The expression of Herceptin using this vector is tested in CHO cells. As shown in FIG. 7, the BMCD chimeric signal peptide is significantly better than AZU (positive control). The expression level from BMCD is about 1.5× that of AZU.

FIG. 7 also shows that a proper sequence of the chimeric signal peptide is important. For example, the BMCD truncated variant (SEQ ID NO:12) with the last two residues (LA) deleted has lost some signal peptide functions, probably because this deletion interferes with the signal peptide cleavage. It is known that the C-region of a signal peptide contains a more polar carboxyl terminus, where the -3 and -1 positions (counting from the signal peptidase cleavage site) typically contain small, aliphatic residues, such as Ala, and are rarely aromatic or charged residues. Therefore, deletion of Leu-Ala from the C-terminus of BMCD might compromise the signal peptidase cleavage and hence interfere with protein secretion.

Figure 8:
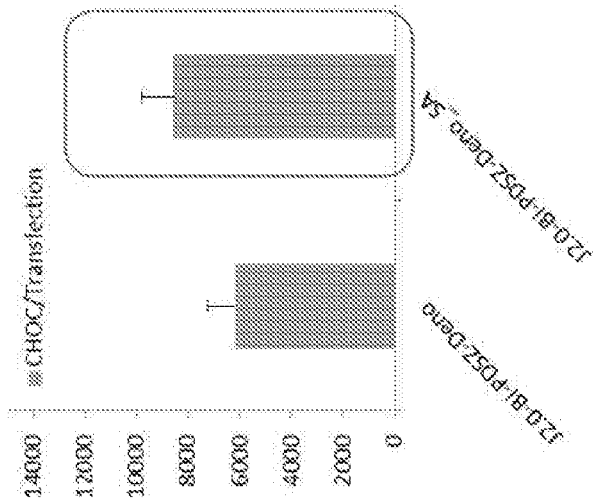
FIG. 8 shows that SEAP_AZU chimeric signal peptide increases the production of Denosumab by about 40%.

While the above results use Herceptin as the target protein/antibody, other proteins (e.g., Avastin, Denosumab, etc.) have also been tested and are found to have similar results. For example, FIG. 8 shows that SEAP_AZU chimeric signal peptide increases the production of Denosumab by about 40%.

Figure 9:
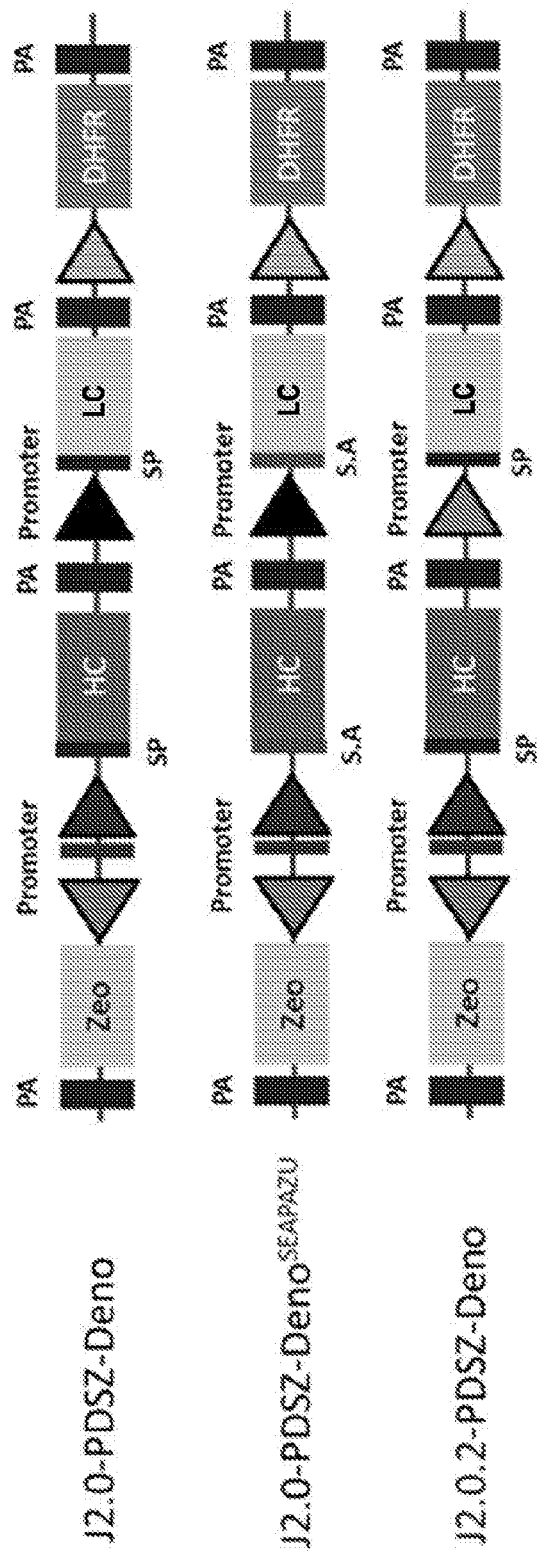
FIG. 9 shows different vectors may impact the efficiencies of a chimeric signal peptide.

In addition to the chimeric signal peptides themselves, the context/environment of these chimeric signal peptides may also have influence on the efficiencies of protein productions. That is, different vectors may further enhance the efficiencies of these chimeric signal peptides. For example, we found that the expression vector J2.0.2 produces about 2 times the level of Denosumab compared to J2.0 vector. Similarly, Avastin also produces better using a J2.0.2 vector. On the other hand, for Herceptin and Tim3 antibodies, the vector J2.0 produces higher yield. J2.0.2 vector has different promotors for the HC and LC chains, as illustrated in FIG. 9. Therefore, the abilities of the chimeric signal peptides to enhance protein production can be further increased by choosing a better vector.

FIGS. 10A-10C show another example of using a J2.0.2 vector to express Denosumab using a SEAP-AZU chimeric signal peptide. FIG. 10A shows a scheme of the cell culture and protein expression. Briefly, CHO cells ($3 \times 10^5$ cells/ml) are seeded in batch culture flasks. After batch culture for 5 to 6 days, the supernatants may be collected and analyzed for the protein production, using ELISA or HPLC. FIG. 10B shows the vector constructs for J2.0.2-PDSB-Deno$^{AZUd}$ and J2.0.2-PDSB-Deno$^{SEAPAZU}$. These vectors contain dihydrofolate reductase (DHFR) genes to facilitate transfected cell lines from CHO cells that lack the DHFR gene. FIG. 10C shows Denosumab productions on day 5 and day 6 for both vectors. The production levels are comparable from these vectors, suggesting that the SEAPAZU chimeric signal peptide is as effective as the positive control AZU.

Figure 11A:
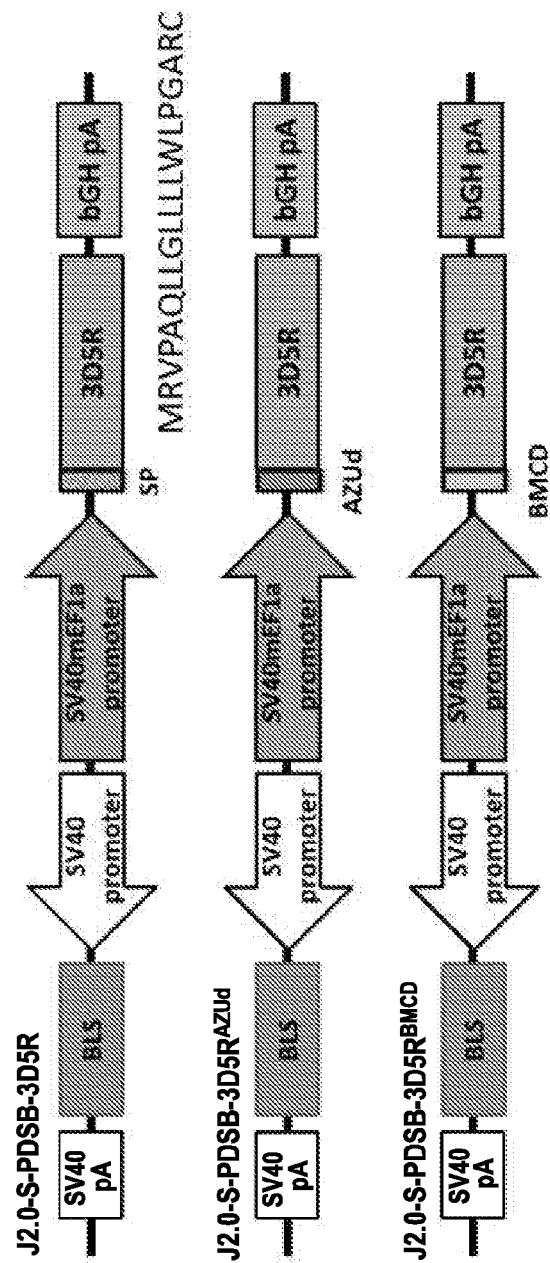
FIG. 11A shows vector constructs for the production of a fusion protein 3D5R using the original signal peptide, AZUd signal peptide, and BMCD signal peptide, respectively.
Figure 11B:
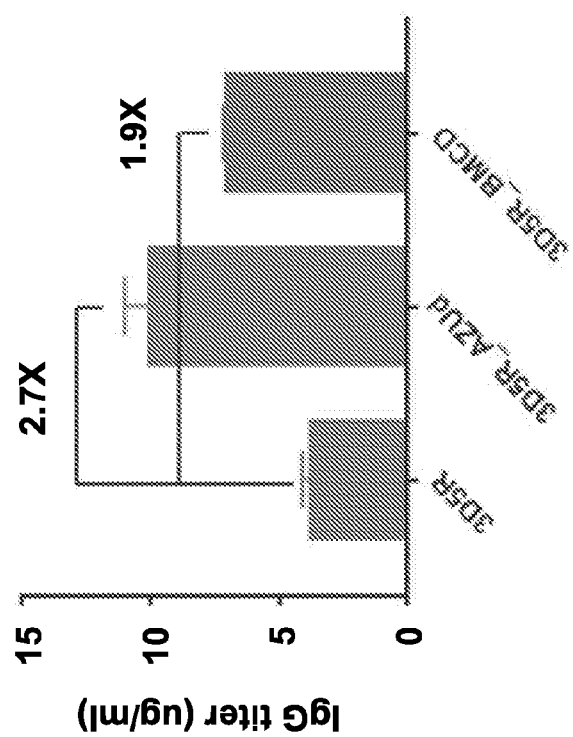
FIG. 11B shows the protein expression levels using the expression vectors of FIG. 11A. The 3D5R fusion protein production level using the AZUd signal peptide is 2.7 times that using the original signal peptide, while that using BMCD is 1.9 times that of the original signal peptide.

While the above examples show the productions of various antibodies, embodiments of the invention may also be used for the productions of other proteins (such as fusion proteins of interest). FIG. 11A shows the expression vector constructs for the production of a fusion protein 3D5R. The three constructs contain the original signal peptide (SP, MRVPAQLLGLLLLWLPGARC, SEQ ID NO:10), AZUd (SEQ ID NO:9), and BMCD (SEQ ID NO:5), respectively. FIG. 11B shows the protein expression results. It is clear that the AZUd signal peptide, which is the AZU signal peptide with 7 amino acid residues deleted from the C-region and was found to be as good as the AZU signal peptide, is efficient in the production and secretion of the 3D5R fusion protein; the production levels is 2.7 times that of the original signal peptide. Similarly, the chimeric signal peptide BMCD is also very efficient, producing 1.9 times the level of the original signal peptide.

Figure 12A:
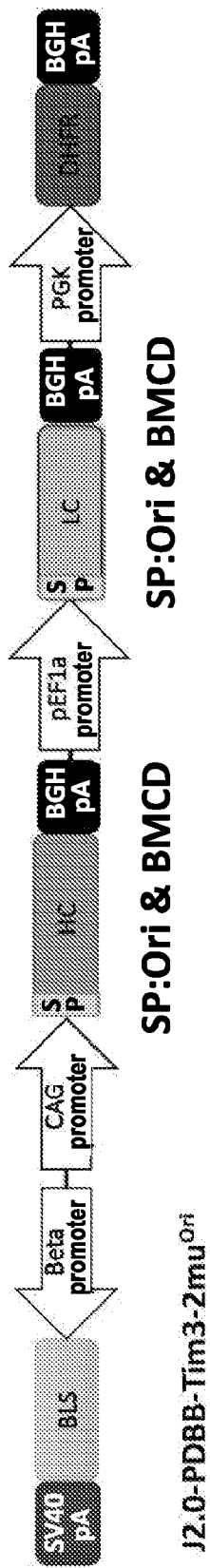
FIG. 12A shows expression vector constructs for the production of antibodies against T-cell immunoglobulin and mucin domain 3 (TIM3), using the original signal peptide or the BMCD chimeric signal peptide.
Figure 12B:
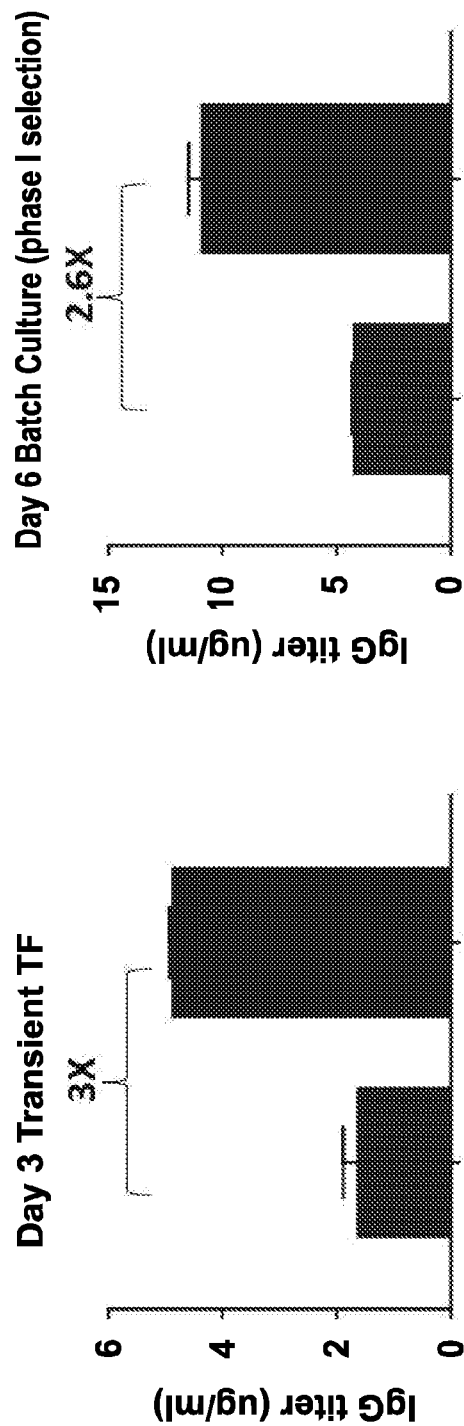
FIG. 12B shows results of protein production using the expression vectors of FIG. 12A. As shown, the BMCD signal peptide produces much higher proteins than the original signal peptide. In transient transfection, the BMCD production levels is 3 times higher than that of the original signal peptide, while in stably transfected cells, the BMCD signal peptide produces a level 2.6 times that of the original signal peptide.

FIGS. 12A and 12B show another example for the production of T-cell immunoglobulin and mucin domain 3 (TIM3) antibody using the J2.0 vector and BMCD signal peptide. FIG. 12A shows the vector constructs, containing either the original signal peptide (ori) or the BMCD signal peptide. FIG. 12B shows the production of TIM3 after 3 days of transient transfection or 6 days after phase I selection of the transfected cells in batch cultures. In both transfection-expression systems, BMCD produces 3 times and 2.6 times the protein expression levels, as compared with the vector using the original signal peptide.

The above examples show that chimeric signal peptides of the invention can efficiently enhanced the production and secretion of recombinant proteins, include antibodies. The enhancements are seen in transient transfection, as well as in stable transfected cells in batch cultures.

Embodiments of the invention may be practiced with any suitable methods known in the art. The following description provides some examples. One skilled in the art would appreciate that these examples are for illustration only and that other modifications and variations are possible without departing from the scope of the invention.

Cell Culture and Media

Chinese Hamster Ovary (CHO) cell lines DXB11 were obtained from Dr. Lawrence Chasin, University of Columbia. The DHFR negative CHO DXB11 cell line (also known as DUX-B11 and DUKX) was historically the first CHO cell line to be used for large scale production of heterologous proteins and is still used for production of a number of complex proteins (C. S. Kaas et al., "Sequencing the CHO DXB11 genome reveals regional variations in genomic stability and haploidy," BMC Genomics, 16, Article No. 160 (2015)). Cell cultures were carried out in an incubator under 5% $CO_2$, at a temperature of 37° C. and 95% humidity. The media for the cell cultures include Hyclone and Mixed medium (50% CDFortiCHO and 50% ActiCHO). Cell counts and viability analysis were performed after staining with trypan blue using an automatic cell counter TC10 (Bio-Rad, USA).

The transfection constructs include puromycin resistance gene. Stable pools were selected based on puromycin resistance. Once it becomes a single clone, selection is not necessary.

Vector Constructions

In the examples, each HC or LC peptide fragment containing the signal peptide sequence may be amplified using PCR and then integrated into expression vectors using any technique known in the art, such as the highly efficacy In-Fusion® HD enzyme (Clontech, Takara Bio USA, Inc., Mountain View, CA). To construct the expression vectors of the invention, a selected signal peptide sequence is cloned into a suitable vector (e.g., pcDNA3.1 or pTCAE based vectors) that contains a protein to be expressed (e.g., HC or LC chain of a target antibody). The vector also contains an IRES sequence for the control of reporter genes (e.g., EGFP and DsRed). Using the CD33 signal peptide as an example, CMV-HC$^{CD33}$-IRES-EGFP and CMV-LC$^{CD33}$-IRES-DsRed were obtained. Other signal peptides may be similarly constructed. For example, the following signal peptide sequences (TABLE 2) have been constructed into expression vectors in a similar manner.

TABLE 2

| SP Name | Sequence | SEQ ID NO |
|---|---|---|
| BM40 | gccaccatgagagcctggatctttttctgctctgcctcgctggcagagccctggct | 13 |
| IL_2 | gccaccatgcagctgctgtcatgcatcgcattgatcttggcgctggtg | 14 |
| HA | gccaccatgaagaccatcatcgccctgtcctacatcttctgcttggtcctcgga | 15 |
| Insulin | gccaccatggcgctgtggatgcgcctgctgccgctgctggcgctgctggcgctgtgg ggcccagatccggcggcggcg | 16 |
| CD33 | gccaccatgccgctgctgctgctgctgccgctgctgtgggcgggcgcgctggcg | 17 |
| IFNA2 | gccaccatggcgctgacctttgcgctgctggtggcgctgctggtgctgagctgcaaa agc | 18 |
| IgG kappa chain | gccaccatggagacagacacactcctgctatgggtactgctgctctgggttccaggt tccactggt | 19 |
| SEAP | atgattctggggccctgcatgctgctgctgctgctgctgggcctgaggctacag ctctccctgggc | 20 |
| CD33-IgK | gccaccatgccgctcctgctatgggtactgctgctctgggcgggcgcgctggcg | 21 |
| IgK-CD33 | gccaccatggagacagacactgctgctgctgccgctgctgtgggttccaggt tccactggt | 22 |
| SEAP-AZU | gccaccatgattctggggcccctgacagtcctggccctgctggctggtctgctgagg ctacagctctccctgggc | 23 |
| AZU-SEAP | gccaccatgacccggtgcatgctgctgctgctgctgggcctggcgtcctcgagg gcc | 24 |
| BM40-CD33 | gccaccatgagagccctgctgctgctgccgctgctgtgggctggcagagccctggct | 25 |
| CD33-BM40 | gccaccatgccgtggatctttttctgctcgcctcgcgggcgcgctggcg | 26 |

The constructions of these vectors may use any conventional cloning techniques. In some specific examples, overlapping PCR techniques are used, e.g., PCR amplifications and joining of amplified overlap fragments. These techniques are routine and conventional.

Transfection of CHO Cells

Transfection of the constructs into host cells can use any suitable methods and setups known in the art. For example, CHOK1 cells were cultured in a 6-well plate. Each well was seeded with 1×10$^6$ cells in 3 mL of Hyclone™ HyCell™ CHO culture medium (GE Healthcare) containing 8 mM GlutaMAX™ (Thermo Fischer). Transfections of the vectors (e.g., pcDNA3.1) containing the LC and HC of Herceptin constructs may be performed using any suitable reagents known in the art, such as a lipophilic agent FreeStyle MAX™ (Thermo Fischer). For example, Herceptin HC$^{BM40CD33}$, Herceptin LC$^{BM40CD33}$, and the transfection reagent Freestyle MAX™ (Thermo Fischer) were separately added into OptiPRO™ SFM (Thermo Fischer) to prepare the vector solutions as shown in TABLE 3. These solutions were let stand for 5 minutes before they were added into the transfection reagents and mixed well. The resultant solutions were allowed to stand for 20 minutes before transfection into the cells. The cells were then evaluated 3 days after the transfection.

TABLE 3

| CHOK1 | Sample ID | pcDNA3.1-HerHC$^{BM40CD33}$ (A) + pcDNA3.1-HerLC$^{BM40CD33}$ (B) | | | TCAE-Her$^{BMCD}$ |
|---|---|---|---|---|---|
| Herceptin | Conc. (μg/μl) | A: 0.83/ B: 0.61 1:4 | A: 0.83/ B: 0.61 1:2 | A: 0.83/ B: 0.61 1:1 | 2 |
| Prepare DNA-Liquid Complex | | | | | |
| Dilute 5 ug DNA in OptiPRO SFM (total 0.15 ml) | Plasmid (μl) | HC: 1.2/ LC: 6.6 | HC: 2/ LC: 5.5 | HC: 3/ LC: 4.1 | 2.5 |
| | Medium (μl) | 142.2 | 142.5 | 142.9 | 147.5 |
| Dilute 5 ul FreeStyle MAX in OptiPRO SFM (total 0.15 ml) | Liposome (μl) | 5 | 5 | 5 | 5 |
| | Medium (μl) | 145 | 145 | 145 | 145 |
| Add the diluted DNA to the diluted reagent Add 3 ml of complex to each suspension flask (3 ml); cell density/ml | Incubate for 20 mins 1.00E+6 | | | | |

Protein Expression

For protein/antibody production in the test CHO cells, the antibody/protein expression constructs may be from commercial sources or be prepared based on procedures known in the art and transfected into the test CHO cells for transient expression of the antibodies or proteins. The transfected CHO cells were cultured for an appropriate duration (e.g., 3 days) to produce the target proteins. Alternatively, the transfection may produce stable cell lines that can be used to produce proteins in conventional cultures or batch cultures. Any methods known in the art to facilitate the selection of stable transfectant cell lines may be used. For example, one may use vectors that contain DHFR genes and CHO cells that lack the DHFR genes. Only the CHO cells containing the transfected vectors would survive in restricted media.

The protein expression levels may be assessed using any suitable methods, such as ELISA, HPLC, or other methods. If the expressed protein has an enzymatic activity (e.g., SEAP), one can also use the activity to assess the protein expression levels. For example, for SEAP, a GreatEscAPe™ chemiluminescence kit may be obtained from Clontech. Prepare 1× Dilution Buffer by diluting the 5× Dilution Buffer 1:5 with ddH$_2$O. To evaluate the protein expression levels, transfer 25 μl of cell culture medium from transfected cells or mock transfected cells to a 96-well microtiter plate. If necessary, the plate can be sealed and frozen at −20° C. for future analysis. Add 75 μl of 1× Dilution Buffer to each sample in the 96-well microtiter plate. Seal the plate with adhesive aluminum foil or a regular 96-well lid and incubate the diluted samples for 30 min at 65° C. using a heat block or water bath.

Cool the samples on ice for 2-3 min, then equilibrate to room temperature. Add 100 μl of SEAP Substrate Solution to each sample. Incubate for 30 min at room temperature before reading. Use a 96-well plate reader luminometer (e.g., CLARIOstar®) to detect and record the chemiluminescence signals. Antibody titers in the culture supernatants were determined by ELISA. Cell specific productivity (Qp) was calculated by dividing the titer by the integral area under the curve of daily viable cell density.

While embodiments of the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A chimeric signal peptide for protein expression, comprising an N-region, a hydrophobic region (H-region), and a C-region, wherein the N-region and the C-region are from a signal peptide of a first protein and the hydrophobic region (H-region) is from a signal peptide of a second protein, wherein the first protein is BM40 and the second protein is CD33.

2. The chimeric signal peptide according to claim 1, wherein the chimeric signal peptide comprises the sequence of SEQ ID NO: 5 or 6.

* * * * *

SEQUENCE LISTING

```
<160> NUMBER OF SEQ ID NOS: 26

<210> SEQ ID NO 1
<211> LENGTH: 16
<212> TYPE: PRT
<213> ORGANISM: Artificial Sequence
<220> FEATURE:
<223> OTHER INFORMATION: Synthetic

<400> SEQUENCE: 1

Met Pro Leu Leu Leu Trp Val Leu Leu Leu Trp Ala Gly Ala Leu Ala
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Synthetic
```

-continued

```
<400> SEQUENCE: 2

Met Glu Thr Asp Thr Leu Leu Leu Leu Pro Leu Leu Trp Val Pro
1               5                   10                  15

Gly Ser Thr Gly
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic

<400> SEQUENCE: 3

Met Ile Leu Gly Pro Leu Thr Val Leu Ala Leu Leu Ala Gly Leu Leu
1               5                   10                  15

Arg Leu Gln Leu Ser Leu Gly
            20

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

Met Thr Arg Cys Met Leu Leu Leu Leu Leu Leu Gly Leu Ala Ser
1               5                   10                  15

Ser Arg Ala

<210> SEQ ID NO 5
<211> LENGTH: 18
<212> TYPE: PRT
<213> ORGANISM: Artificial Sequence
<220> FEATURE:
<223> OTHER INFORMATION: Synthetic

<400> SEQUENCE: 5

Met Arg Ala Leu Leu Leu Leu Pro Leu Leu Trp Ala Gly Arg Ala
1               5                   10                  15

Leu Ala

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Met Pro Trp Ile Phe Phe Leu Leu Cys Leu Ala Gly Ala Leu Ala
1               5                   10                  15

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Met Ile Leu Gly Pro Cys Met Leu Leu Leu Leu Leu Leu Gly Leu
1               5                   10                  15
```

Arg Leu Gln Leu Ser Leu Gly
            20

<210> SEQ ID NO 8
<211> LENGTH: 26
<212> TYPE: PRT
<213> ORGANISM: Artificial Sequence
<220> FEATURE:
<223> OTHER INFORMATION: Synthetic

<400> SEQUENCE: 8

Met Thr Arg Leu Thr Val Leu Ala Leu Leu Ala Gly Leu Leu Ala Ser
1               5                   10                  15

Ser Arg Ala Gly Ser Ser Pro Leu Leu Asp
            20                  25

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

Met Thr Arg Leu Thr Val Leu Ala Leu Leu Ala Gly Leu Leu Ala Ser
1               5                   10                  15

Ser Arg Ala

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Met Arg Val Pro Ala Gln Leu Leu Gly Leu Leu Leu Leu Trp Leu Pro
1               5                   10                  15

Gly Ala Arg Cys
            20

<210> SEQ ID NO 11
<211> LENGTH: 26
<212> TYPE: PRT
<213> ORGANISM: Artificial Sequence
<220> FEATURE:
<223> OTHER INFORMATION: Synthetic

<400> SEQUENCE: 11

Met Pro Leu Leu Leu Trp Val Leu Leu Leu Trp Ala Gly Ala Leu Ala
1               5                   10                  15

Glu Val Gln Leu Val Glu Ser Gly Gly Gly
            20                  25

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Met Arg Ala Leu Leu Leu Leu Pro Leu Leu Trp Ala Gly Arg Ala
1               5                   10                  15

```
<210> SEQ ID NO 13
<211> LENGTH: 57
<212> TYPE: DNA
<213> ORGANISM: Artificial Sequence
<220> FEATURE:
<223> OTHER INFORMATION: Synthetic

<400> SEQUENCE: 13
gccaccatga gagcctggat cttttttctg ctctgcctcg ctggcagagc cctggct    57

<210> SEQ ID NO 14
<211> LENGTH: 48
<212> TYPE: DNA
<213> ORGANISM: Artificial Sequence
<220> FEATURE:
<223> OTHER INFORMATION: Synthetic

<400> SEQUENCE: 14
gccaccatgc agctgctgtc atgcatcgca ttgatcttgg cgctggtg              48

<210> SEQ ID NO 15
<211> LENGTH: 54
<212> TYPE: DNA
<213> ORGANISM: Artificial Sequence
<220> FEATURE:
<223> OTHER INFORMATION: Synthetic

<400> SEQUENCE: 15
gccaccatga agaccatcat cgccctgtcc tacatcttct gcttggtcct cgga       54

<210> SEQ ID NO 16
<211> LENGTH: 78
<212> TYPE: DNA
<213> ORGANISM: Artificial Sequence
<220> FEATURE:
<223> OTHER INFORMATION: Synthetic

<400> SEQUENCE: 16
gccaccatgg cgctgtggat gcgcctgctg ccgctgctgg cgctgctggc gctgtggggc    60
ccagatccgg cggcggcg                                                  78

<210> SEQ ID NO 17
<211> LENGTH: 54
<212> TYPE: DNA
<213> ORGANISM: Artificial Sequence
<220> FEATURE:
<223> OTHER INFORMATION: Synthetic

<400> SEQUENCE: 17
gccaccatgc cgctgctgct gctgctgccg ctgctgtggg cgggcgcgct ggcg         54

<210> SEQ ID NO 18
<211> LENGTH: 60
<212> TYPE: DNA
<213> ORGANISM: Artificial Sequence
<220> FEATURE:
<223> OTHER INFORMATION: Synthetic

<400> SEQUENCE: 18
gccaccatgg cgctgaccct tgcgctgctg gtggcgctgc tggtgctgag ctgcaaaagc    60

<210> SEQ ID NO 19
<211> LENGTH: 66
<212> TYPE: DNA
```

<213> ORGANISM: Artificial Sequence
<220> FEATURE:
<223> OTHER INFORMATION: Synthetic

<400> SEQUENCE: 19
gccaccatgg agacagacac actcctgcta tgggtactgc tgctctgggt tccaggttcc    60
actggt    66

<210> SEQ ID NO 20
<211> LENGTH: 69
<212> TYPE: DNA
<213> ORGANISM: Artificial Sequence
<220> FEATURE:
<223> OTHER INFORMATION: Synthetic

<400> SEQUENCE: 20
atgattctgg ggccctgcat gctgctgctg ctgctgctgc tgggcctgag gctacagctc    60
tccctgggc    69

<210> SEQ ID NO 21
<211> LENGTH: 54
<212> TYPE: DNA
<213> ORGANISM: Artificial Sequence
<220> FEATURE:
<223> OTHER INFORMATION: Synthetic

<400> SEQUENCE: 21
gccaccatgc cgctcctgct atgggtactg ctgctctggg cgggcgcgct ggcg    54

<210> SEQ ID NO 22
<211> LENGTH: 66
<212> TYPE: DNA
<213> ORGANISM: Artificial Sequence
<220> FEATURE:
<223> OTHER INFORMATION: Synthetic

<400> SEQUENCE: 22
gccaccatgg agacagacac actgctgctg ctgctgccgc tgctgtgggt tccaggttcc    60
actggt    66

<210> SEQ ID NO 23
<211> LENGTH: 75
<212> TYPE: DNA
<213> ORGANISM: Artificial Sequence
<220> FEATURE:
<223> OTHER INFORMATION: Synthetic

<400> SEQUENCE: 23
gccaccatga ttctggggcc cctgacagtc ctggccctgc tgctggtct gctgaggcta    60 cagctctccc tgggc    75

<210> SEQ ID NO 24
<211> LENGTH: 63
<212> TYPE: DNA
<213> ORGANISM: Artificial Sequence
<220> FEATURE:
<223> OTHER INFORMATION: Synthetic

<400> SEQUENCE: 24
gccaccatga cccggtgcat gctgctgctg ctgctgctgc tgggcctggc gtcctcgagg    60
gcc    63

```
<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25
gccaccatga gagccctgct gctgctgctg ccgctgctgt gggctggcag agccctggct      60

<210> SEQ ID NO 26
<211> LENGTH: 50
<212> TYPE: DNA
<213> ORGANISM: Artificial Sequence
<220> FEATURE:
<223> OTHER INFORMATION: Synthetic

<400> SEQUENCE: 26
gccaccatgc cgtggatctt ttttctgctc gcctcgcggg cgcgctggcg                 50
```